United States Patent [19]
Marini et al.

[11] Patent Number: 5,804,290
[45] Date of Patent: Sep. 8, 1998

[54] MONOAXIALLY STRETCHED MOLDED ARTICLE MADE OF POLYTETRAFLUOROETHYLENE

[75] Inventors: Ingo Marini, Lenzing; Adalbert Wimmer, Vöcklabruck; Josef Bachmair, Seewalchen, all of Austria

[73] Assignee: Lenzing Aktiengesellschaft, Lenzing, Austria

[21] Appl. No.: 481,244

[22] PCT Filed: Sep. 28, 1994

[86] PCT No.: PCT/AT94/00139

§ 371 Date: Jun. 7, 1995

§ 102(e) Date: Jun. 7, 1995

[87] PCT Pub. No.: WO95/12698

PCT Pub. Date: May 11, 1995

[30] Foreign Application Priority Data

Nov. 3, 1993 [AT] Austria ..................................... 2221/93

[51] Int. Cl.⁶ .............................. D02G 3/00; B32B 27/00; B27J 5/00; B29C 49/08
[52] U.S. Cl. .......................... 428/220; 428/364; 428/401; 428/421; 264/127; 264/288.4
[58] Field of Search .............................. 132/321; 428/364, 428/401, 421, 220; 264/127, 288.4

[56] References Cited

U.S. PATENT DOCUMENTS

| | | |
|---|---|---|
| 2,893,105 | 7/1959 | Lauterbach . |
| 2,933,154 | 4/1960 | Lauterbach . |
| 3,556,161 | 1/1971 | Roberts .................................... 138/141 |
| 3,943,949 | 3/1976 | Ashton et al. ............................. 132/89 |
| 3,953,566 | 4/1976 | Gore ........................................ 264/288 |
| 3,985,934 | 10/1976 | Farrissey, Jr. et al. .................. 428/397 |
| 4,025,598 | 5/1977 | Sasshofer et al. ....................... 264/140 |
| 4,096,227 | 6/1978 | Gore ..................................... 264/210 R |
| 4,163,825 | 8/1979 | Wimmer ................................. 428/368 |
| 4,414,990 | 11/1983 | Yost ......................................... 132/91 |
| 4,596,837 | 6/1986 | Yamamoto et al. .................... 521/145 |
| 4,776,358 | 10/1988 | Lorch ..................................... 132/321 |
| 5,033,488 | 7/1991 | Curtis et al. ............................ 132/321 |
| 5,167,890 | 12/1992 | Sasshofer et al. ..................... 264/127 |
| 5,209,251 | 5/1993 | Curtis et al. ........................... 132/321 |
| 5,220,932 | 6/1993 | Blass ...................................... 132/321 |
| 5,225,131 | 7/1993 | Tamaru et al. ......................... 264/113 |
| 5,413,127 | 5/1995 | Hill ........................................ 132/321 |
| 5,511,791 | 4/1996 | Ebisuno ................................. 473/354 |
| 5,518,012 | 5/1996 | Dolan et al. ........................... 132/321 |

FOREIGN PATENT DOCUMENTS

| | | |
|---|---|---|
| 340561 | 12/1977 | Austria . |
| 347003 | 12/1978 | Austria . |
| 370674 | 4/1983 | Austria . |
| 391473B | 10/1990 | Austria . |
| 119185A2 | 9/1984 | European Pat. Off. . |
| 335466A2 | 10/1989 | European Pat. Off. . |
| 391887A2 | 10/1990 | European Pat. Off. . |
| 2025835 | 1/1980 | United Kingdom . |
| 9010673 | 9/1990 | WIPO . |

*Primary Examiner*—Mark Chapman
*Attorney, Agent, or Firm*—Baker & Botts LLP

[57] ABSTRACT

Monoaxially stretched moulded article made of polytetrafluorethylene (PTFE) containing talc and/or mica and/or a high temperature resistant polyimide and/or whiting as filler, and having strength values in the stretching direction of at least 10 cN/tex.

The moulded article according to the invention may be formed into dental floss if it contains whiting as filler.

21 Claims, No Drawings

MONOAXIALLY STRETCHED MOLDED ARTICLE MADE OF POLYTETRAFLUOROETHYLENE

BACKGROUND OF THE INVENTION

The invention relates to a monoaxially stretched moulded article made of polytetrafluorethylene (PTFE) which may be shaped as a film, tape, yarn or fibre, and relates to a process for its production.

Because of its thermal stability and its chemical inertness, PTFE is a valued material. AT-B 370,674 discloses monoaxially stretched films made of sintered PTFE which in the stretch direction have values for strength of between 50N/mm$^2$ and 140N/mm$^2$. These films are produced by first pressing PTFE powder to form a cylindrical moulded article. Subsequently the moulded article is sintered, whereupon films are peeled off, heated to temperatures of at least 327° C. and stretched.

GB-A-2 025 835 describes the production of porous PTFE moulded articles by the paste-extrusion process, a pasty composition, containing essentially PTFE powder and a lubricant (hydrocarbon), being forced through dies, whereupon the lubricant is removed by drying. Then the moulded article is heated to above the crystallite melting point of the PTFE (327° C.) and stretched during heating.

AT-B 391.473 discloses a process for the production of monoaxially stretched moulded articles made of PTFE, a pasty PTFE composition being continually processed to form a moulding which is led over a plurality of rollers or rolls and is heated and stretched, the moulding, before application of the stretching, being heated to a temperature between 327° and 450° C. and sintered. This process permits the production of monoaxially stretched moulded articles from PTFE with strength values in the stretching direction of at least 22 cN/tex (500 N/mm$^2$).

It is known that PTFE multifilament yarns produced by matrix spinning according to U.S. Pat. Nos. 2,893,105 and 2,933,154 and those produced by the gap peel process of AT-B-340,561 can be used to produce plait cords for packing glands. From AT-B-347,003 it is further known how to coat such yarns with PTFE and graphite to improve the sliding characteristics.

It is also known that oriented but not sintered film tapes produced by means of paste extrusion, impregnated with PTFE dispersant and lubricated with paraffin oil are used for the manufacture of packing glands. These film tapes are also commercially available when containing graphite fillings.

All these products filled with graphite have the drawback that the graphite filling, which is provided to increase the sliding characteristics, is of black colour, whereby these products cannot be used in certain areas of the industry. In addition, these products exhibit a high tendency to flow (cold flow) which naturally increases wear. It is a further drawback that the moulded articles monoaxially stretched and filled with graphite solely have strength values of less than 10 cN/tex.

SUMMARY OF THE INVENTION

The present invention aims to eliminate these drawbacks, to broaden the applicability of the PTFE material and to provide a monoaxially stretched moulded article having a light colour and a higher strength and a lower cold flow tendency than a moulded PTFE article filled with graphite. It should further be feasible to produce said moulded PTFE article having different sliding characteristics.

The monoaxially stretched moulded article made of polytetrafluorethylene (PTFE) according to the present invention is characterized in that it contains talc and/or mica and/or a high temperature resistant polyimide and/or whiting as filler, and has strength values of at least 10 cN/tex and preferably more than 16 cN/tex. As high temperature resistant polyimides those disclosed in EP-A-0 119 185 and in U.S. Pat. No. 3,985,934 are particularly suited.

It has surprisingly been successful to mix PTFE powder by means of paste extrusion with said fillers and to process it to e.g. films, to sinter these films and to stretch them subsequently, whereby very high strength values can be achieved despite the presence of the filler. The strength values of e.g. an unfilled PTFE yarn (produced according to AT-B-370,674) are between 5 and 15 cN/tex, whereas a filled yarn produced according to the present invention has strength values up to 25 cN/tex. The moulded article according to the present invention may contain filler up to 40% by weight. Decreasing tensile strength at break is accompanied by decreasing elongation at break and increasing creep resistance, which is an important feature for using the yarns as sealing for packing glands.

The moulded article according to the present invention may contain up to 40% by weight filler without going beyond the indicated minimum strength of 10 cN/tex.

BRIEF DESCRIPTION OF THE PREFERRED EMBODIMENTS

A preferred embodiment of the moulded article according to the present invention is characterized in that it contains as filler talc and/or mica and/or a high temperature resistant polyimide of between 20 and 30% by weight. Such a moulded article exhibits good sliding characteristics. Measurements done according to DIN 53 375 revealed that yarns made of pure PTFE exhibit kinetic friction values ($\mu_p$) of about 150 (110–200), yarns having graphite as filler exhibit values of between 50 and 100 and yarns according to the present invention having talc as filler exhibit values of between 30 and 70.

If the moulded article according of the present invention further has advantageously an elongation of not more than 30% it is excellent suited as e.g. material in pumps for sealing the shaft (within the casing of the packing gland). Heretofore moulded PTFE articles with graphite fillings have been used for that purpose. These known moulded articles exhibit an unsufficient creep resistance and a high wear thereby abrasion being of black colour in case of graphite filling leaks from the casing of the packing gland and might undesirably discolour and contaminate e.g. a light coloured liquid to be sealed. The present embodiment of the moulded article according to the invention does not show any of these drawbacks.

If the moulded article according to the invention is formed as a yarn it can be used advantageously for the production of plait sealings.

A further preferred embodiment of the moulded article according to the present invention is characterized in that it contains as filler whiting of at least 5% by weight. It has been shown that whiting increases the kinetic friction $\mu_p$ to at least 200, so that such a material is well suited for all uses wherein a high kinetic friction is required.

A preferred embodiment of the moulded article according to the present invention is characterized in that it contains solely whitning as filler and that it is in the form of dental floss. It has been shown that using the dental floss according to the present invention preserves the gum more than it is the case with dental floss of the prior art. By adjusting the amount of whiting the kinetic friction of the dental floss can be modified. Experiments have revealed that dental floss containing whiting from 0,1 to 15% by weight is particularly well suited.

The invention further relates to a process for the production of a moulded article according to the invention, said process being characterized by the combination of the following features that a) polytetrafluorethylene powder is mixed with talc and/or mica and/or a high temperature resistant polyimide and/or whiting and a hydrocarbon, b) the mixture obtained is formed into a pre-shaped article and freed from the hydrocarbon, c) the pre-shaped article freed from hydrocarbon is sintered and subsequently stretched in the sintered state.

The filler is preferably used in such an amount that 40% by weight are not exceeded in the moulded article.

The pre-shaped article is heated to a temperature of at least 327° C. and preferably of between 380° and 400° C. for being sintered.

To achieve the indicated strength values of the moulded article according to the present invention the sintered pre-shaped article preferably is stretched at a ratio of between 1:5 and 1:20 and preferably of between 1:5 and 1:15.

In a particular embodiment of the process according to the present invention the pre-shaped article is a film which is cut into tapes after having been sintered and stretched, and these tapes are conveniently subjected to a fibrillation treatment by means of a needle roller.

Preferred embodiments of the present invention are illustrated in more detail by way of the following examples. The moulded articles of the present invention are produced using a sinter and stretching equipment disclosed in AT-B 391.473.

EXAMPLE 1

100 parts by weight of commercially available PTFE powder Hostaflon TF 2029 of Höchst AG are mixed with 25 parts talc (Naintsch A-30) and 30 parts of a lubricant normally used in paste extrusion (hydrocarbon exhibiting a boiling range of 186°–214° C.) and pressed to cylindrical moulded articles. These cylindrical articles subsequently are pressed into a strand, are further rolled into a film and are freed from lubricant by drying. The dried film is sintered at a temperature of 385° C. and then stretched at a ratio of 1:7. A surprisingly soft film (30–38 Shore D) exhibiting good sliding characteristics and a strength of 21,3 cN/tex at an elongation of 6,5% is obtained.

EXAMPLE 2

70 parts PTFE powder of the type Hostaflon TF 2029 are mixed with 30 parts talc A-30 and 30 parts lubricant and are rolled to a film, dried, sintered and stretched the same way as in Example 1. The strength is 19,5 cN/tex at an elongation of 5,5%.

EXAMPLE 3

A mixture described in Example 1 is processed to a film the same way as in Example 1 but being sintered at 395° C. and then stretched at a ratio of 1:8,5. The strength value is 24,5 cN/tex at an elongation of 5%. Then the film is subjected to a fibrillation treatment and soaked with 22% paraffin oil.

The final product is in a way a multifilament yarn which can be directly processed to plait cords. The paraffin oil serves as lubricant.

EXAMPLE 4

100 parts PTFE powder of the type Algoflon DF 200 (producer: Ausimont S.p.A.) are mixed with 47 parts talc A-60 and 30 parts lubricant and processed into a film. Said film is sintered at 390° C. and stretched at a ratio of 1:6. The strength of the film obtained is 16 cN/tex at an elongation of 8%.

EXAMPLE 5

A mixture as described in Example 4 is processed into a film the same way but sintered at 395° C. and stretched at a ratio of 1:7. The strength is 17,5 cN/tex at an elongation of 5%. After stretching the film is further fibrillated and soaked with 20% paraffin oil.

EXAMPLE 6

75 parts PTFE powder of the type Hostaflon TF 2029 are mixed with 25 parts mica and 27 parts lubricant and processed to a film and stretched the same way as described in Example 1. The strength is 16,5 cN/tex at an elongation of 8,5%.

EXAMPLE 7

100 parts PTFE powder of the type Algoflon DF 200 are mixed with 10 parts whiting and 25 parts lubricant and processed into a film. Said film is sintered at 390° C. and stretched at a ratio of 1:13,5 and cut into tapes. The strength of the tapes obtained is 26 cN/tex at an elongation of 4,5%. By incorporating whiting the kinetic friction of that product is increased. The product may be used as dental floss.

We claim:

1. A monoaxially stretched molded article which comprises polytetrafluorethylene (PTFE) and one or more fillers selected from the group consisting of talc, mica, a high temperature resistant polyamide, whiting and combinations thereof, wherein the molded article has been sintered and has a strength value in the stretching direction of at least 10 cN/tex.

2. A molded article according to claim 1, wherein the molded article comprises not more than 40% by weight filler.

3. A molded article according to claim 2, wherein the filler is selected from the group consisting of talc, mica, a high temperature resistant polyamide and combinations thereof, wherein the molded article contains from 20 to 30% by weight filler.

4. A molded article according to claim 2, comprising at least 5% by weight whiting.

5. A molded article according to claim 1, 2, 3 or 4, wherein the molded article has an elongation of not more than 30%.

6. A molded article according to claim 2, wherein the filler is whiting, and wherein the molded article is in the form of dental floss.

7. A molded article according to claim 6, wherein the molded article comprises from 0.1 to 15% by weight whiting.

8. A process for the production of a monoaxially stretched molded article as in claim 1 which comprises:

a) mixing polytetrafluoroethylene powder with a hydrocarbon and one or more fillers selected from the group consisting of talc, mica, a high temperature resistant polyimide, and whiting, to obtain a mixture;

b) shaping the mixture into a pre-shaped article;

c) removing the hydrocarbon from the mixture;

d) sintering the pre-shaped article; and e) stretching the sintered pre-shaped article.

9. A process according to claim 8, wherein the molded article comprises not more than 40% by weight filler.

10. A process according to claim 9, wherein the filler is selected from the group consisting of talc, mica, a high temperature resistant polyimide and combinations thereof, wherein the molded article contains from 20 to 30% by weight filler.

11. A process according to claim 9, wherein the molded article comprises at least 5% by weight whiting.

12. A process according to claim 8, 9, 10 or 11, wherein the molded article has an elongation of not more than 30%.

13. A process according to claim 9, wherein the filler is whiting, and wherein the molded article is in the form of dental floss.

14. A process according to claim 13, wherein the molded article comprises from 0.1 to 15% by weight whiting.

15. A process according to claim 8, wherein the pre-shaped article is sintered by heating the pre-shaped article to a temperature of at least 327° C.

16. A process according to claim 1, wherein the pre-shaped article is sintered by heating the pre-shaped article to a temperature between 380° and 400° C.

17. A process according to claim 8, wherein sintered pre-shaped article is stretched at a ratio of between 1:5 and 1:20.

18. A process according to claim 17, wherein the pre-shaped article is stretched at a ratio of between 1:5 and 1:15.

19. A process according to claim 8, wherein the pre-shaped article is a film which is cut into tapes after the sintering and stretching the pre-shaped article.

20. A process according to claim 19, further comprising subjecting the tapes to a fibrillation treatment.

21. A monoaxially stretched molded article formed by the process comprising mixing polytetrafluoroethylene powder with a hydrocarbon and one or more fillers selected from the group consisting of talc, mica, a high temperature resistant polyimide, and whiting, to obtain a mixture, shaping the mixture into a pre-shaped article, sintering the pre-shaped article, and stretching the sintered pre-shaped article.

* * * * *